US010716676B2

(12) United States Patent
Tornier et al.

(10) Patent No.: US 10,716,676 B2
(45) Date of Patent: Jul. 21, 2020

(54) METHOD FOR MODELING A GLENOID SURFACE OF A SCAPULA, APPARATUS FOR IMPLANTING A GLENOID COMPONENT OF A SHOULDER PROSTHESIS, AND METHOD FOR PRODUCING SUCH A COMPONENT

(71) Applicant: Tornier SAS, Montbonnot Saint Martin (FR)

(72) Inventors: Alain Tornier, Saint Ismier (FR); Delphine Claire Michelle Henry, Saint Ismier (FR)

(73) Assignee: Tornier SAS, Montbonnot Saint Martin (FR)

( * ) Notice: Subject to any disclaimer, the term of this patent is extended or adjusted under 35 U.S.C. 154(b) by 472 days.

(21) Appl. No.: 14/576,801

(22) Filed: Dec. 19, 2014

(65) Prior Publication Data

US 2015/0105787 A1 Apr. 16, 2015

Related U.S. Application Data

(62) Division of application No. 12/489,092, filed on Jun. 22, 2009, now Pat. No. 8,932,361.

(30) Foreign Application Priority Data

Jun. 20, 2008 (FR) ...................................... 08 54092

(51) Int. Cl.
*A61F 2/46* (2006.01)
*A61F 2/30* (2006.01)
(Continued)

(52) U.S. Cl.
CPC .......... *A61F 2/30942* (2013.01); *A61B 90/36* (2016.02); *A61F 2/4081* (2013.01);
(Continued)

(58) Field of Classification Search
CPC .......... A61F 2/4612; A61F 2002/30943; A61F 2002/4635
See application file for complete search history.

(56) References Cited

U.S. PATENT DOCUMENTS

| 4,919,670 | A | 4/1990 | Dale et al. |
| 5,030,219 | A | 7/1991 | Matsen, III et al. |
(Continued)

FOREIGN PATENT DOCUMENTS

| CA | 2927086 | 4/2015 |
| CA | 2927811 | 4/2015 |
(Continued)

OTHER PUBLICATIONS

US 9,451,972 B2, 09/2016, Lang et al. (withdrawn)
(Continued)

*Primary Examiner* — Nicholas W Woodall
(74) *Attorney, Agent, or Firm* — Knobbe, Martens, Olson & Bear, LLP

(57) ABSTRACT

An apparatus and modeling method of the present invention includes the successive steps of generating cartographic data representative of points belonging to a glenoid surface; distinguishing from among the cartographic data a first group of cartographic data corresponding to a first part of the glenoid surface, the first surface part being situated farthest down in the vertical direction in relation to the scapula; calculating from the first group of cartographic data a first ellipsoid portion that coincides substantially with the first surface part; and obtaining a theoretical glenoid surface from the first ellipsoid portion. By virtue of the theoretical glenoid surface obtained by this method, it is possible to assist the surgeon in optimizing the position of implantation
(Continued)

of a glenoid component and to produce a glenoid component "made to measure" for the scapula that is to be fitted with a prosthesis.

22 Claims, 5 Drawing Sheets

(51) Int. Cl.
*A61F 2/40* (2006.01)
*G06T 17/05* (2011.01)
*G06T 17/30* (2006.01)
*A61B 90/00* (2016.01)
*A61B 34/20* (2016.01)

(52) U.S. Cl.
CPC .......... *A61F 2/4612* (2013.01); *A61F 2/4657* (2013.01); *G06T 17/05* (2013.01); *G06T 17/30* (2013.01); *A61B 34/20* (2016.02); *A61B 2034/2068* (2016.02); *A61F 2002/30884* (2013.01); *A61F 2002/30943* (2013.01); *A61F 2002/30952* (2013.01); *A61F 2002/4632* (2013.01); *A61F 2002/4633* (2013.01); *A61F 2002/4658* (2013.01); *G06T 2210/41* (2013.01)

(56) References Cited

U.S. PATENT DOCUMENTS

| | | |
|---|---|---|
| 5,329,846 A | 7/1994 | Bonutti |
| 5,383,938 A | 1/1995 | Rohr et al. |
| 5,531,793 A | 7/1996 | Kelman et al. |
| 5,610,966 A | 3/1997 | Martell et al. |
| 5,725,586 A | 3/1998 | Sommerich |
| 5,768,134 A | 6/1998 | Swaelens et al. |
| 5,769,856 A | 6/1998 | Dong et al. |
| 5,779,710 A | 7/1998 | Matsen, III |
| 5,807,437 A | 9/1998 | Sachs et al. |
| 5,824,078 A | 10/1998 | Nelson et al. |
| 5,824,085 A | 10/1998 | Sahay et al. |
| 6,002,859 A | 12/1999 | DiGioia, III et al. |
| 6,129,764 A | 10/2000 | Servidio |
| 6,172,856 B1 | 1/2001 | Jang |
| 6,183,519 B1 | 2/2001 | Bonnin et al. |
| 6,364,910 B1 | 4/2002 | Shultz et al. |
| 6,385,475 B1 | 5/2002 | Cinquin et al. |
| 6,432,142 B1 | 8/2002 | Kamiya et al. |
| 6,459,948 B1 | 10/2002 | Ateshian et al. |
| 6,648,894 B2 | 11/2003 | Abdelgany et al. |
| 6,772,026 B2 | 8/2004 | Bradbury et al. |
| 6,797,006 B2 | 9/2004 | Hodorek |
| 6,915,150 B2 | 7/2005 | Cinquin et al. |
| 6,944,518 B2 | 9/2005 | Roose |
| 7,468,075 B2 | 12/2008 | Lang et al. |
| 7,469,474 B2 | 12/2008 | Farrar |
| 7,534,263 B2 | 5/2009 | Burdulis, Jr. et al. |
| 7,599,539 B2 | 10/2009 | Kunz et al. |
| 7,618,451 B2 | 11/2009 | Berez et al. |
| 7,634,119 B2 | 12/2009 | Tsougarakis et al. |
| 7,648,530 B2 | 1/2010 | Habermeyer et al. |
| 7,717,956 B2 | 5/2010 | Lang |
| 7,747,305 B2 | 6/2010 | Dean et al. |
| 7,796,791 B2 | 9/2010 | Tsougarakis et al. |
| 7,799,077 B2 | 9/2010 | Lang et al. |
| 7,802,503 B2 | 9/2010 | Couvillion et al. |
| 7,822,588 B2 | 10/2010 | Mueller et al. |
| 7,831,079 B2 | 11/2010 | Kunz et al. |
| 7,927,338 B2 | 4/2011 | Laffargue et al. |
| 7,981,158 B2 | 7/2011 | Fitz et al. |
| 7,983,777 B2 | 7/2011 | Melton et al. |
| 8,007,448 B2 | 8/2011 | Barrera |
| 8,014,984 B2 | 9/2011 | Iannotti et al. |
| 8,055,487 B2 | 11/2011 | James |
| 8,062,302 B2 | 11/2011 | Lang et al. |
| 8,066,708 B2 | 11/2011 | Lang et al. |
| 8,077,950 B2 | 12/2011 | Tsougarakis et al. |
| 8,083,745 B2 | 12/2011 | Lang et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,234,097 B2 | 7/2012 | Steines et al. |
| 8,337,501 B2 | 12/2012 | Fitz et al. |
| 8,337,503 B2 | 12/2012 | Lian |
| 8,337,507 B2 | 12/2012 | Lang et al. |
| 8,343,218 B2 | 1/2013 | Lang et al. |
| 8,350,186 B2 | 1/2013 | Jones et al. |
| 8,366,771 B2 | 2/2013 | Burdulis, Jr. et al. |
| 8,377,073 B2 | 2/2013 | Wasielewski |
| 8,377,129 B2 | 2/2013 | Fitz et al. |
| 8,439,926 B2 | 5/2013 | Bojarski et al. |
| 8,457,930 B2 | 6/2013 | Schroeder |
| 8,460,304 B2 | 6/2013 | Fitz et al. |
| 8,475,463 B2 | 7/2013 | Lian |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski et al. |
| 8,532,806 B1 | 9/2013 | Masson |
| 8,535,319 B2 | 9/2013 | Ball |
| 8,545,509 B2 | 10/2013 | Park et al. |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,731,885 B2 | 5/2014 | Iannotti et al. |
| 8,735,773 B2 | 5/2014 | Lang |
| 8,744,148 B2 | 6/2014 | Nord et al. |
| 8,768,028 B2 | 7/2014 | Lang et al. |
| 8,771,365 B2 | 7/2014 | Bojarski et al. |
| 8,774,900 B2 * | 7/2014 | Buly ................. A61B 5/1121 600/427 |
| 8,775,133 B2 | 7/2014 | Schroeder |
| 8,814,942 B2 | 8/2014 | Anthony et al. |
| 8,843,229 B2 | 9/2014 | Vanasse et al. |
| 8,864,769 B2 | 10/2014 | Stone et al. |
| 8,882,847 B2 | 11/2014 | Burdulis, Jr. et al. |
| 8,884,618 B2 | 11/2014 | Mahfouz |
| 8,888,855 B2 | 11/2014 | Roche et al. |
| 8,898,043 B2 | 11/2014 | Ashby et al. |
| 8,906,107 B2 | 12/2014 | Bojarski et al. |
| 8,926,706 B2 | 1/2015 | Bojarski et al. |
| 8,932,361 B2 | 1/2015 | Tornier et al. |
| 8,932,363 B2 | 1/2015 | Tsougarakis et al. |
| 8,934,961 B2 | 1/2015 | Lakin et al. |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,088 B2 | 2/2015 | Tsougarakis et al. |
| 8,971,606 B2 | 3/2015 | Chaoui |
| 8,974,539 B2 | 3/2015 | Bojarski et al. |
| 8,984,731 B2 | 3/2015 | Broeck et al. |
| 8,989,460 B2 | 3/2015 | Mahfouz |
| 8,992,538 B2 | 3/2015 | Keefer |

(56) References Cited

U.S. PATENT DOCUMENTS

| | | |
|---|---|---|
| 8,998,915 B2 | 4/2015 | Fitz et al. |
| 9,020,788 B2 | 4/2015 | Lang |
| 9,023,050 B2 | 5/2015 | Lang et al. |
| 9,055,953 B2 | 6/2015 | Lang et al. |
| 9,060,788 B2 | 6/2015 | Bollinger |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,126,673 B1 | 9/2015 | Green et al. |
| 9,180,015 B2 | 11/2015 | Fitz et al. |
| 9,186,161 B2 | 11/2015 | Lang et al. |
| 9,186,254 B2 | 11/2015 | Fitz et al. |
| 9,211,199 B2 | 12/2015 | Ratron |
| 9,216,025 B2 | 12/2015 | Fitz et al. |
| 9,220,516 B2 | 12/2015 | Lang et al. |
| 9,220,517 B2 | 12/2015 | Lang et al. |
| 9,232,955 B2 | 1/2016 | Bonin, Jr. et al. |
| 9,237,950 B2 | 1/2016 | Hensley et al. |
| 9,241,724 B2 | 1/2016 | Lang et al. |
| 9,241,725 B2 | 1/2016 | Lang et al. |
| 9,278,413 B2 | 3/2016 | Sperling |
| 9,295,481 B2 | 3/2016 | Fitz et al. |
| 9,295,482 B2 | 3/2016 | Fitz et al. |
| 9,301,768 B2 | 4/2016 | Buza et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 9,320,608 B2 | 4/2016 | Sperling |
| 9,320,620 B2 | 4/2016 | Bojarski et al. |
| 9,326,780 B2 | 5/2016 | Wong et al. |
| 9,333,085 B2 | 5/2016 | Fitz et al. |
| 9,351,743 B2 | 5/2016 | Kehres et al. |
| 9,358,018 B2 | 6/2016 | Fitz et al. |
| 9,381,025 B2 | 7/2016 | Fitz et al. |
| 9,381,026 B2 | 7/2016 | Trouilloud et al. |
| 9,387,083 B2 | 7/2016 | Al Hares et al. |
| 9,402,726 B2 | 8/2016 | Linderman et al. |
| 9,408,615 B2 | 8/2016 | Fitz et al. |
| 9,408,616 B2 | 8/2016 | Kehres et al. |
| 9,408,686 B1 | 8/2016 | Miller et al. |
| 9,414,928 B2 | 8/2016 | Sperling |
| 9,439,767 B2 | 9/2016 | Bojarski et al. |
| 9,486,226 B2 | 11/2016 | Chao |
| 9,495,483 B2 | 11/2016 | Steines et al. |
| 9,517,134 B2 | 12/2016 | Lang |
| 9,539,013 B2 | 1/2017 | Katrana et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,603,711 B2 | 3/2017 | Bojarski et al. |
| 9,636,229 B2 | 5/2017 | Lang et al. |
| 9,646,113 B2 | 5/2017 | Park et al. |
| 9,662,214 B2 | 5/2017 | Li et al. |
| 9,668,873 B2 | 6/2017 | Winslow et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,700,420 B2 | 7/2017 | Fitz et al. |
| 9,700,971 B2 | 7/2017 | Lang |
| 9,713,533 B2 | 7/2017 | Taylor et al. |
| 9,715,563 B1 | 7/2017 | Schroeder |
| 9,717,508 B2 | 8/2017 | Iannotti et al. |
| 9,737,367 B2 | 8/2017 | Steines et al. |
| 9,741,263 B2 | 8/2017 | Iannotti et al. |
| 9,770,335 B2 | 9/2017 | Sperling |
| 9,775,680 B2 | 10/2017 | Bojarski et al. |
| 9,849,019 B2 | 12/2017 | Miller et al. |
| 9,872,773 B2 | 1/2018 | Lang et al. |
| 9,877,790 B2 | 1/2018 | Bojarski et al. |
| 9,895,230 B2 | 2/2018 | Mahfouz |
| 9,913,723 B2 | 3/2018 | Fitz et al. |
| 9,937,046 B2 | 4/2018 | Mahfouz |
| 9,943,370 B2 | 4/2018 | Asseln et al. |
| 9,956,047 B2 | 5/2018 | Bojarski et al. |
| 9,956,048 B2 | 5/2018 | Bojarski et al. |
| 9,993,341 B2 | 6/2018 | Vanasse et al. |
| 10,085,839 B2 | 10/2018 | Wong et al. |
| 10,405,993 B2 | 9/2019 | Deransart et al. |
| 2001/0047210 A1 | 11/2001 | Wolf |
| 2002/0007294 A1 | 1/2002 | Bradbury et al. |
| 2002/0025358 A1 | 2/2002 | Nelson et al. |
| 2002/0082741 A1 | 6/2002 | Mazumder et al. |
| 2003/0139818 A1 | 7/2003 | Rogers et al. |
| 2004/0064189 A1 | 4/2004 | Maroney et al. |
| 2004/0102866 A1 | 5/2004 | Harris et al. |
| 2004/0133276 A1 | 7/2004 | Lang et al. |
| 2004/0171924 A1* | 9/2004 | Mire .................. G06F 19/3437 600/407 |
| 2004/0181144 A1 | 9/2004 | Cinquin et al. |
| 2004/0243481 A1 | 12/2004 | Bradbury et al. |
| 2005/0049709 A1 | 3/2005 | Tornier |
| 2005/0065617 A1 | 3/2005 | Barrera et al. |
| 2005/0065628 A1 | 3/2005 | Roose |
| 2005/0112397 A1 | 5/2005 | Rolfe et al. |
| 2005/0197814 A1 | 9/2005 | Aram et al. |
| 2005/0216305 A1 | 9/2005 | Funderud |
| 2006/0136058 A1 | 6/2006 | Pietrzak |
| 2007/0089518 A1 | 4/2007 | Ericson et al. |
| 2007/0118055 A1 | 5/2007 | McCombs |
| 2007/0118243 A1 | 5/2007 | Schroeder et al. |
| 2007/0191741 A1 | 8/2007 | Tsai et al. |
| 2007/0244563 A1 | 10/2007 | Roche et al. |
| 2007/0249967 A1 | 10/2007 | Buly et al. |
| 2008/0014082 A1 | 1/2008 | Kunz et al. |
| 2008/0140209 A1 | 6/2008 | Iannotti et al. |
| 2008/0183297 A1 | 7/2008 | Boileau et al. |
| 2008/0228269 A1 | 9/2008 | McLeod et al. |
| 2008/0243127 A1 | 10/2008 | Lang et al. |
| 2008/0269906 A1* | 10/2008 | Iannotti ............... A61F 2/30942 623/19.11 |
| 2009/0226068 A1 | 9/2009 | Fitz et al. |
| 2009/0264894 A1 | 10/2009 | Wasielewski |
| 2009/0292464 A1* | 11/2009 | Fuchs .................. G06Q 10/087 701/532 |
| 2009/0318929 A1 | 12/2009 | Tornier et al. |
| 2010/0087927 A1 | 4/2010 | Roche et al. |
| 2010/0191100 A1* | 7/2010 | Anderson ............... A61B 5/055 600/424 |
| 2010/0217270 A1 | 8/2010 | Polinski et al. |
| 2010/0303313 A1 | 12/2010 | Lang et al. |
| 2011/0029088 A1 | 2/2011 | Raucher et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0119884 A1 | 5/2011 | Ratron |
| 2011/0282403 A1 | 11/2011 | Anthony et al. |
| 2012/0078258 A1 | 3/2012 | Lo et al. |
| 2012/0116203 A1 | 5/2012 | Vancraen et al. |
| 2012/0130434 A1 | 5/2012 | Stemniski |
| 2012/0141034 A1* | 6/2012 | Iannotti ............... A61B 17/1739 382/199 |
| 2012/0143267 A1 | 6/2012 | Iannotti et al. |
| 2012/0253350 A1 | 10/2012 | Anthony et al. |
| 2012/0276509 A1 | 11/2012 | Iannotti et al. |
| 2012/0279933 A1 | 11/2012 | Hensler et al. |
| 2013/0053968 A1 | 2/2013 | Nardini et al. |
| 2013/0110116 A1 | 5/2013 | Kehres et al. |
| 2013/0110470 A1 | 5/2013 | Vanasse et al. |
| 2013/0110471 A1 | 5/2013 | Lang et al. |
| 2013/0114873 A1 | 5/2013 | Chaoui |
| 2013/0172898 A1 | 7/2013 | Iannotti et al. |
| 2013/0190882 A1 | 7/2013 | Humphrey |
| 2013/0211531 A1 | 8/2013 | Steines et al. |
| 2013/0261629 A1 | 10/2013 | Anthony et al. |
| 2013/0274752 A1 | 10/2013 | Trouilloud et al. |
| 2013/0338673 A1 | 12/2013 | Keppler |
| 2014/0039633 A1 | 2/2014 | Roche et al. |

(56) References Cited

U.S. PATENT DOCUMENTS

| | | |
|---|---|---|
| 2014/0257499 A1 | 9/2014 | Winslow et al. |
| 2014/0276867 A1 | 9/2014 | Kelley et al. |
| 2014/0371863 A1 | 12/2014 | Vanasse et al. |
| 2015/0045903 A1 | 2/2015 | Neal |
| 2015/0054195 A1 | 2/2015 | Greyf |
| 2015/0093283 A1 | 4/2015 | Miller et al. |
| 2015/0150688 A1 | 6/2015 | Vanasse et al. |
| 2015/0223941 A1 | 8/2015 | Lang |
| 2015/0250552 A1 | 9/2015 | Radermacher et al. |
| 2015/0250597 A1 | 9/2015 | Lang et al. |
| 2015/0320430 A1 | 11/2015 | Kehres et al. |
| 2015/0328004 A1 | 11/2015 | Mafhouz |
| 2016/0015466 A1 | 1/2016 | Park et al. |
| 2016/0051367 A1 | 2/2016 | Gervasi et al. |
| 2016/0067049 A1 | 3/2016 | Flaherty et al. |
| 2016/0074052 A1 | 3/2016 | Keppler et al. |
| 2016/0100907 A1 | 4/2016 | Gomes |
| 2016/0120555 A1 | 5/2016 | Bonin, Jr. et al. |
| 2016/0143744 A1 | 5/2016 | Bojarski et al. |
| 2016/0143749 A1 | 5/2016 | Holovacs et al. |
| 2016/0157937 A1 | 6/2016 | Kehres et al. |
| 2016/0166392 A1 | 6/2016 | Vanasse et al. |
| 2016/0184104 A1 | 6/2016 | Sperling |
| 2016/0193051 A1 | 7/2016 | Budhabhatti et al. |
| 2016/0213385 A1 | 7/2016 | Iannotti et al. |
| 2016/0242933 A1 | 8/2016 | Deransart et al. |
| 2016/0256222 A1 | 9/2016 | Walch |
| 2016/0270854 A1 | 9/2016 | Chaoui et al. |
| 2016/0296285 A1 | 10/2016 | Chaoui et al. |
| 2016/0296290 A1 | 10/2016 | Furrer et al. |
| 2016/0324648 A1 | 11/2016 | Hodorek et al. |
| 2016/0331467 A1 | 11/2016 | Slamin et al. |
| 2016/0345987 A1 | 12/2016 | Guilloux et al. |
| 2016/0374697 A1 | 12/2016 | Kehres et al. |
| 2017/0000614 A1 | 1/2017 | Mahfouz |
| 2017/0000615 A1 | 1/2017 | Mahfouz |
| 2017/0027587 A1 | 2/2017 | Fraone et al. |
| 2017/0027593 A1 | 2/2017 | Bojarski et al. |
| 2017/0056024 A1 | 3/2017 | Chao |
| 2017/0079803 A1 | 3/2017 | Lang |
| 2017/0105841 A1 | 4/2017 | Vanasse et al. |
| 2017/0105843 A1 | 4/2017 | Britton et al. |
| 2017/0112626 A1 | 4/2017 | Miller et al. |
| 2017/0119531 A1 | 5/2017 | Bojarski et al. |
| 2017/0151058 A1 | 6/2017 | Sperling |
| 2017/0216038 A1 | 8/2017 | Lang et al. |
| 2017/0231783 A1 | 8/2017 | Lang et al. |
| 2017/0249440 A1 | 8/2017 | Lang et al. |
| 2017/0258598 A1 | 9/2017 | Radermacher et al. |
| 2017/0273795 A1 | 9/2017 | Neichel et al. |
| 2017/0273800 A1 | 9/2017 | Emerick et al. |
| 2017/0273801 A1 | 9/2017 | Hodorek |
| 2017/0281357 A1 | 10/2017 | Taylor et al. |
| 2017/0296347 A1 | 10/2017 | Chua et al. |
| 2017/0304063 A1 | 10/2017 | Hatzidakis et al. |
| 2017/0360567 A1 | 12/2017 | Fitz et al. |
| 2017/0367766 A1 | 12/2017 | Mahfouz |
| 2017/0367828 A1 | 12/2017 | Steines et al. |
| 2017/0367834 A1 | 12/2017 | Fitz et al. |
| 2018/0028325 A1 | 2/2018 | Bojarski et al. |
| 2018/0161176 A1 | 6/2018 | Vivanz et al. |
| 2018/0228614 A1 | 8/2018 | Lang et al. |
| 2018/0235706 A1 | 8/2018 | Asseln et al. |
| 2018/0235762 A1 | 8/2018 | Radermacher et al. |
| 2018/0263782 A1 | 9/2018 | Lang et al. |
| 2018/0289380 A1 | 10/2018 | Mauldin et al. |
| 2019/0015113 A1 | 1/2019 | Morvan |
| 2019/0015116 A1 | 1/2019 | Neichel et al. |
| 2019/0015117 A1 | 1/2019 | Neichel et al. |
| 2019/0015118 A1 | 1/2019 | Neichel et al. |
| 2019/0015119 A1 | 1/2019 | Athwal et al. |
| 2019/0015221 A1 | 1/2019 | Neichel et al. |
| 2019/0038360 A1 | 2/2019 | Chaoui |
| 2019/0343658 A1 | 11/2019 | Deransart et al. |

FOREIGN PATENT DOCUMENTS

| | | |
|---|---|---|
| CA | 2938709 | 5/2015 |
| DE | 10 2006 047663 | 4/2008 |
| EP | 1 249 213 | 10/2002 |
| EP | 1 563 810 | 8/2005 |
| EP | 1 265 555 B1 | 11/2005 |
| EP | 1 862 151 | 12/2007 |
| EP | 1 902 689 | 3/2008 |
| EP | 1 952 788 | 8/2008 |
| EP | 2135576 | 12/2009 |
| EP | 1 917 051 B1 | 6/2010 |
| EP | 2 243 445 | 10/2010 |
| EP | 2 324 801 A1 | 5/2011 |
| EP | 2 501 313 | 9/2012 |
| EP | 2 544 601 | 1/2013 |
| EP | 2583242 | 4/2013 |
| EP | 2 653 136 | 10/2013 |
| EP | 2 845 547 | 3/2015 |
| EP | 2 965 720 | 1/2016 |
| EP | 3057518 | 8/2016 |
| EP | 3057524 | 8/2016 |
| EP | 3065671 | 9/2016 |
| EP | 3068317 | 9/2016 |
| EP | 2 874 570 B1 | 1/2017 |
| EP | 3 117 801 | 1/2017 |
| FR | 2 579 454 | 10/1986 |
| FR | 2 859 099 | 3/2005 |
| FR | 2962573 A1 | 1/2012 |
| FR | 2982694 B1 | 11/2016 |
| FR | 2982979 B1 | 11/2016 |
| FR | 2982693 B1 | 12/2016 |
| GB | 2501494 A | 10/2013 |
| WO | WO 93/025157 | 12/1993 |
| WO | WO 00/35346 | 6/2000 |
| WO | WO 00/59411 | 10/2000 |
| WO | WO 02/061688 | 8/2002 |
| WO | WO 2010/120346 | 10/2010 |
| WO | WO 2011/110374 | 9/2011 |
| WO | WO 2011/154891 | 12/2011 |
| WO | WO 2011/157961 | 12/2011 |
| WO | WO 2012/021241 | 2/2012 |
| WO | WO 2012/058349 | 5/2012 |
| WO | WO 2012/125319 | 9/2012 |
| WO | WO 2013/060851 | 5/2013 |
| WO | WO 2013/062848 | 5/2013 |
| WO | WO 2013/062851 | 5/2013 |
| WO | WO 2013/142998 | 10/2013 |
| WO | WO 2014/020561 | 2/2014 |
| WO | WO 2014/035991 | 3/2014 |
| WO | WO 2014/180972 | 11/2014 |
| WO | WO 2015/052586 | 4/2015 |
| WO | WO 2015/056097 | 4/2015 |
| WO | WO 2015/068035 | 5/2015 |
| WO | WO 2015/071757 | 5/2015 |
| WO | WO 2015/175397 | 11/2015 |
| WO | WO 2015/185219 | 12/2015 |
| WO | WO 2017/005514 | 1/2017 |
| WO | WO 2017/007565 | 1/2017 |
| WO | WO 2017/091657 | 6/2017 |
| WO | WO 2017/105815 | 6/2017 |
| WO | WO 2017/106294 | 6/2017 |
| WO | WO 2017/184792 | 10/2017 |
| WO | WO 2017/214537 | 12/2017 |
| WO | WO 2018/022227 | 2/2018 |
| WO | WO 2019/014278 | 1/2019 |
| WO | WO 2019/014281 | 1/2019 |
| WO | WO 2019/033037 | 2/2019 |
| WO | WO 2019/060780 | 3/2019 |

OTHER PUBLICATIONS

European Search Report issued in EP Application No. 10191949, dated Apr. 14, 2011, 9 pages.

French Opinion issued in FR Application No. 1050541, dated Jan. 27, 2010, 5 pages.

French Search Report issued in FR Application No. 1050541, dated Sep. 15, 2010, 2 pages.

(56) References Cited

OTHER PUBLICATIONS

Search Report issued in French Application No. 08 54092, dated Feb. 9, 2009, in 8 pages.
Boileau, et al., "The three-dimensional geometry of the proximal humerus: implications for surgical technique and prosthetic design." The Journal of bone and joint surgery. British vol. 79.5 (1997): 857-865.
Dougherty, "Digital Image Processing for Medical Applications," May 11, 2009 (May 11, 2009), Cambridge University Press, XP002615721.
Gregory, et al., "Accuracy of Glenoid Component Placement in Total Shoulder Arthroplasty and Its Effect on Clinical and Radiological Outcome in a Retrospective, Longitudinal, Monocentric Open Study," PLOS One, p. e75791, Aug. 1, 2013, vol. 8, No. 10.
Habets, et al., Computer assistance in orthopaedic surgery. Technische Universiteit Eindhoven, 2002.
Hempfing, et al. "Surgical landmarks to determine humeral head retrotorsion for hemiarthroplasty in fractures." Journal of shoulder and elbow surgery 10.5 (2001): 460-463.
Iannotti et al., "Prosthetic positioning in total shoulder arthroplasty," Journal of Shoulder and Elbow Surgery, Jan. 1, 2005, vol. 14, No. 1S, pp. S111-S121.
Kobashi et al., "Knowledge-Based Organ Identification from CT Images," Pattern Recognition, Elsevier, GB, vol. 28, No. 4, Apr. 1, 1995 (Apr. 1, 1995), pp. 475-491, XP004013165.
Lee, C.C. et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003 (Sep. 1, 2003) pp. 208-217, XP011100536.
Ma, et al., "Robust registration for computer-integrated orthopedic surgery: laboratory validation and clinical experience." Medical image analysis 7.3 (2003): 237-250.
"Olympia Total Shoulder System Surgical Technique", Wright Medical Technology, 2001, in 19 pages.
Radermacher, K., et al., "Computer Assisted Orthopaedic Surgery with Image Based Individual Templates," Clinical Orthopaedics and Related Research, No. 354, Sep. 1998, pp. 28-38.
Radermacher, K., et al., "Image Guided Orthopedic Surgery Using Individual Templates: Experimental Results and Aspects of the Development of a Demonstrator for Pelvis Surgery", Health Care Sector, Telematics Applications Program, 1997, pp. 606-615.
Tornier, "Salto Talaris, Total Ankle Prosthesis", 2009.
Valstar, et al. "Towards computer-assisted surgery in shoulder joint replacement." ISPRS journal of photogrammetry and remote sensing 56.5-6 (2002): 326-337.
Valstar, et al. "The use of Roentgen stereophotogrammetry to study micromotion of orthopaedic implants." ISPRS journal of photogrammetry and remote sensing 56.5-6 (2002): 376-389.
Welsh, et al., "CT-based preoperative analysis of scapula morphology and glenohumeral joint geometry." Computer Aided Surgery 8.5 (2003): 264-268.
Wu, et al. "An interface for the data exchange between CAS and CAD/CAM systems." International Congress Series. vol. 1256. Elsevier, 2003.
Zimmer, "Zimmer ® PSI Shoulder Trabecular MetalTM Reverse Glenoid Base Plate Surgical Technique", Dec. 30, 2013.
Favre, et al., "Influence of component positioning on impingement in conventional total shoulder arthroplasty," Clinical Biomechanics, Butterworth Scientifics, Nov. 5, 2007, pp. 174-183, vol. 23, No. 2, Guilford, GB.
Hernigou, et al., "Determining humeral retroversion with computed tomography." Journal of bone and joint surgery. Oct. 2002;84-A(10):1753-62.
Nguyen, et al., "A New Segmentation Method for MRI Images of the Shoulder Joint", Computer and Robot Vision, 2007. CRV '07. Fourth Canadian Conference on, IEEE, PI, May 1, 2007 (May 1, 2007), pp. 329-338, XP031175821.
Tamez-Pena et al., "The Integration of Automatic Segmentation and Motion Tracking for 4D Reconstruction and Visualization of Musculoskeletal Structures," Biomedical Image Analysis, 1998. Proceedings. Workshop on Santa Barbara, CA US, Jun. 26-27, 1998, Los Alamitos, CA, USA, IEEE Comput. Soc. US, Jun. 26, 1998 (Jun. 26, 1998), pp. 154-163, XP010291418.
"Zimmer® PSI Shoulder Planning", Zimmer Biomet TV, posted Jul. 11, 2014, retrieved from internet on Jan. 9, 2020, <https://zimmerbiomet.tv/videos/1025?a=surgeon&version=1190>.

* cited by examiner

METHOD FOR MODELING A GLENOID SURFACE OF A SCAPULA, APPARATUS FOR IMPLANTING A GLENOID COMPONENT OF A SHOULDER PROSTHESIS, AND METHOD FOR PRODUCING SUCH A COMPONENT

CROSS-REFERENCE TO RELATED APPLICATION

The present application is a divisional of U.S. application Ser. No. 12/489,092, filed Jun. 22, 2009, which claims the benefit of French application no. FR 0854092, entitled "GMCAO appliquée à l'épaule", filed Jun. 20, 2008, the complete disclosure of which is hereby incorporated by reference.

TECHNICAL FIELD

The present invention relates to a method of modeling a glenoid surface of a scapula. The present invention also relates to a surgical apparatus and a surgical method for implanting a glenoid component of a shoulder prosthesis. The present invention additionally relates to a glenoid component and a corresponding method for producing such a glenoid component.

BACKGROUND

A surgical operation in which the glenoid articular surface of a scapula is replaced by a concave glenoid prosthetic component is a difficult procedure, particularly because of the ligaments around the shoulder. It has been found that, depending on the geometry of the articulation and/or the position of implantation of such a glenoid component, the glenoid component may be at risk of coming loose on account of the change in forces that are applied to the glenoid component during subsequent movements of the shoulder that has been fitted with the prosthesis.

Currently, orthopedic surgeons select a glenoid component from a plurality of implants having geometries, especially sizes, that differ slightly from one another. They choose the glenoid component by empirically estimating the position of implantation of the selected glenoid component by visually assessing the geometry of the glenoid surface of the patient being operated on. The surgeon seeks to select the prosthetic component and implant it on the scapula in such a way that this component reproduces the original articular glenoid surface of the patient. However, this method can be imprecise, in particular, when the original glenoid cavity of the patient is too badly damaged to provide an indicator that can be directly exploited by surgical observation.

SUMMARY

In one embodiment, the present invention is a modeling method including the successive steps of generating cartographic data representative of points belonging to a glenoid surface; distinguishing from among the cartographic data a first group of cartographic data corresponding to a first part of the glenoid surface, the first surface part being situated farthest down in the vertical direction in relation to the scapula; calculating from the first group of cartographic data a first ellipsoid portion that coincides substantially with the first surface part; and obtaining a theoretical glenoid surface from the first ellipsoid portion.

By virtue of the theoretical glenoid surface obtained by this method, it is possible to assist the surgeon in optimizing the position of implantation of a glenoid component and to produce a glenoid component "made to measure" for the scapula that is to be fitted with a prosthesis.

In another embodiment, the present invention is a surgical apparatus for implanting a glenoid component of a shoulder prosthesis. The apparatus includes position-finding means for spatially locating a scapula of a patient, mapping means for mapping a glenoid surface of the scapula, modeling means for obtaining a theoretical glenoid surface from cartographic data of the glenoid surface supplied by the mapping means, first means of determination for determining a spatial position of a lower reference point for implanting the glenoid component from the cartographic data obtained at a lower end of the glenoid surface by the mapping means, and means of implantation for obtaining a spatial implantation configuration of the glenoid component from at least the theoretical glenoid surface and the lower reference point.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
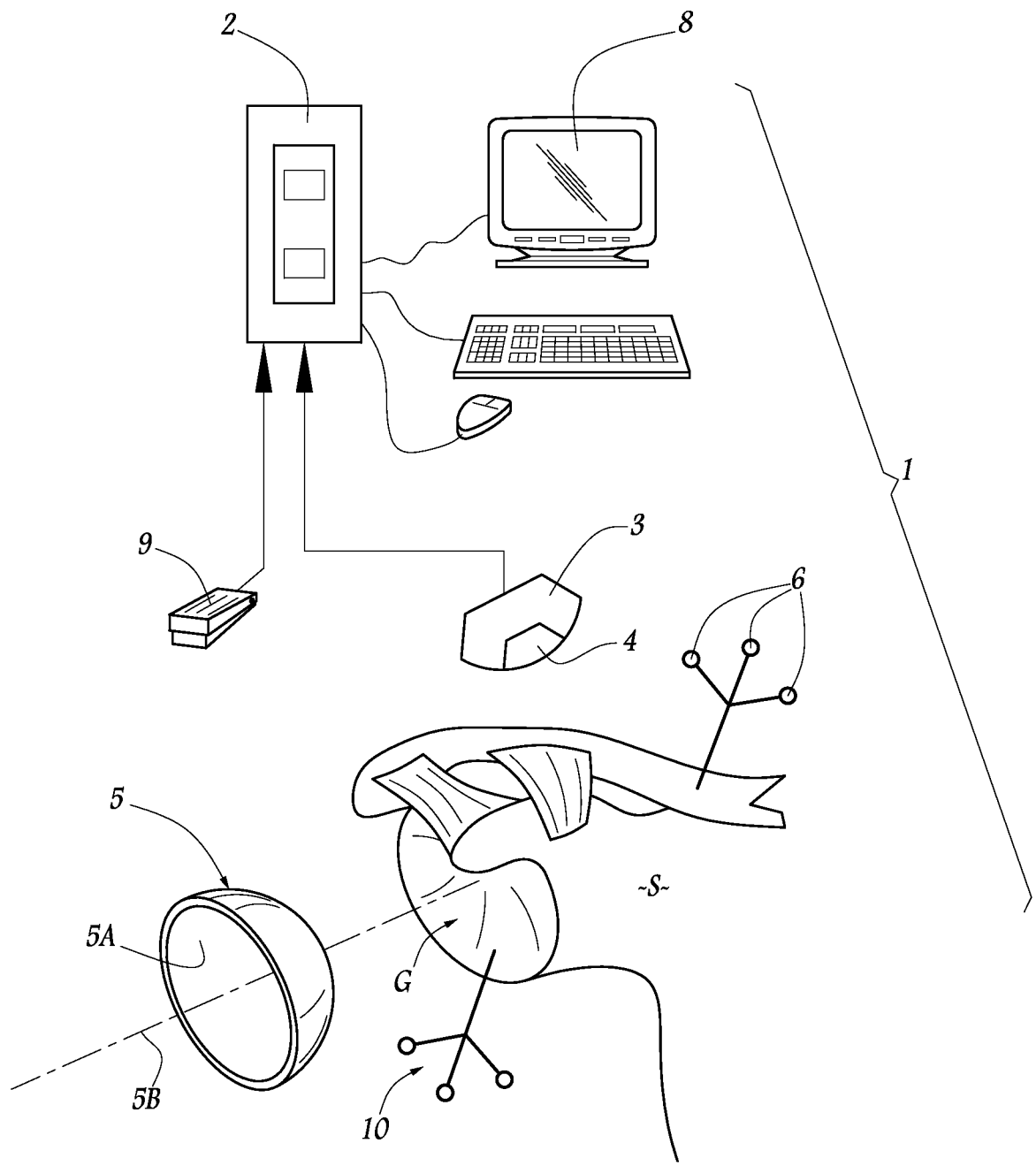
FIG. 1 is a schematic view of an implantation apparatus according to the present invention, applied to the scapula of a patient.

FIG. 1 shows a schematic view of an implantation or surgical apparatus 1 according to the present invention used on the scapula S of a patient to be operated on with a view to implanting a glenoid component. Using the surgical apparatus 1, a glenoid surface G of a scapula S can be modeled to help the surgeon optimize the position of implantation of a glenoid component and/or to produce a glenoid component that is better adapted to a scapula that is to be fitted with a prosthesis, especially in the presence of a glenoid cavity that is in a state of advanced degeneration. The underlying concept of the present invention is based on the realization that, in the vast majority of surgical cases, the degeneration of the glenoid cavity of a patient is often situated in the upper and posterior region of the glenoid surface. Thus, the present invention proposes that only the part of the degenerated glenoid surface situated farthest down the scapula is used to obtain, by modeling, a theoretical glenoid surface as similar as possible to the glenoid surface prior to degeneration.

Estimating a theoretical glenoid surface by modeling has advantages in relation to optimizing the position of implantation of a pre-existing glenoid component and, independently of this, producing a glenoid component specifically adapted to the scapula of a patient. Thus, the present invention further relates to a surgical apparatus and a surgical method for implanting a glenoid component of a shoulder prosthesis and to a method for producing a glenoid component for a scapula. In practice, the modeling method according to the present invention is implemented by any suitable means known in the art, and in particular by computing means The surgical apparatus 1 includes a computer 2 linked to a unit for emitting and receiving infrared radiation. The unit includes a sensor 3 connected to the computer 2 and an infrared source 4 covering the operating field, in which the scapula S of a patient to be treated is shown in part. The scapula S is associated generally with tendons and ligaments and delimits the glenoid surface G on its lateral surface. The glenoid surface G shows degeneration, or partial damage by wear on account of the advanced age and/or a disease of the patient who is being operated on. As will be explained in detail below, the surgical apparatus 1 is designed to aid a surgeon implanting a prosthetic glenoid component 5 in order to replace the degenerated glenoid surface G. In the embodiment shown in FIG. 1, the glenoid component 5 has an overall cup shape and defines an articular face 5A of substantially spherical geometry, defining an axis of revolution 5B. The glenoid component 5 described above is given only by way of example, and other prosthetic glenoid components of different geometries and/or types can be implanted using the surgical apparatus 1 and in accordance with the surgical implantation method described below.

To spatially locate the bone of the scapula S on the computer 2, the surgical apparatus 1 includes a group of markers 6 which passively return infrared radiation in the direction of the sensor 3. The group of markers 6 forms a three-dimensional marking system allowing the assembly composed of the computer 2 and the sensor 3 to follow the spatial position and movement of the scapula S. The use of such markers is well known in the field of computer-aided orthopedics, for example, as described in document EP-A-1 249 213, such that these markers will not be further described here.

The computer 2 is also linked to a screen 8 for displaying information useful to the surgeon, for example, information relating to the location of the scapula S. In one embodiment, the screen 8 may be a video screen. The surgical apparatus 1 also includes control means 9, for example in the form of a pedal, that can be actuated by the surgeon's foot. The surgical apparatus 1 also includes other components, the details of which will be given below in an example of how the surgical apparatus 1 is used to implant the glenoid component 5. By convention, throughout this document, the spatial positioning terms, such as the words "upper", "lower", "vertical", "horizontal" etc., are understood in their anatomical sense, as if the patient being operated on is standing upright on a plane surface.

In a first step, the surgeon makes a plurality of incisions in the soft parts of the patient's shoulder and collects a number of data relating, among other things, to the anatomical geometry of the bone of the patient's scapula S. To this end, various means of acquisition of the data are conceivable. By way of example, the surgeon uses a tracer 10 whose position is located by an assembly composed of the computer 2 and the sensor 3 and which is calibrated in advance. The tracer 10 is applied to various locations on the scapula S, in particular to the whole of the glenoid surface G. The surgeon, by actuating the control means 9, causes the computer 2 to record the position of the tracer 10. From this data, and in some embodiments, from pre-recorded data relating to the basic geometry of the scapula of a human being, the computer 2 is able to establish a three-dimensional map of the degenerated glenoid surface G of the scapula S.

There are other possible ways by which the cartographic data relating to the anatomical geometry of the glenoid surface G can be acquired, for example by extracting such data from pre-operative images of the scapula S of the patient. In one embodiment, the cartographic data can be obtained from scanner images. Such data can also be combined with data obtained by tracing as described above, and combining the data, where appropriate, with predetermined data from databases available in the field of surgery of the shoulder.

At the end of this first step, the computer 2 displays the mapping results on the screen 8, particularly for visual monitoring by the surgeon. This display is effected in particular in a frontal plane with respect to the patient, passing through the mapping points belonging to the glenoid surface G and respectively situated at the far top and far bottom, as is illustrated in FIG. 2, in which the far bottom and the far top mapping points are designated by $P_1$ and $P_2$, respectively.

Figure 2:
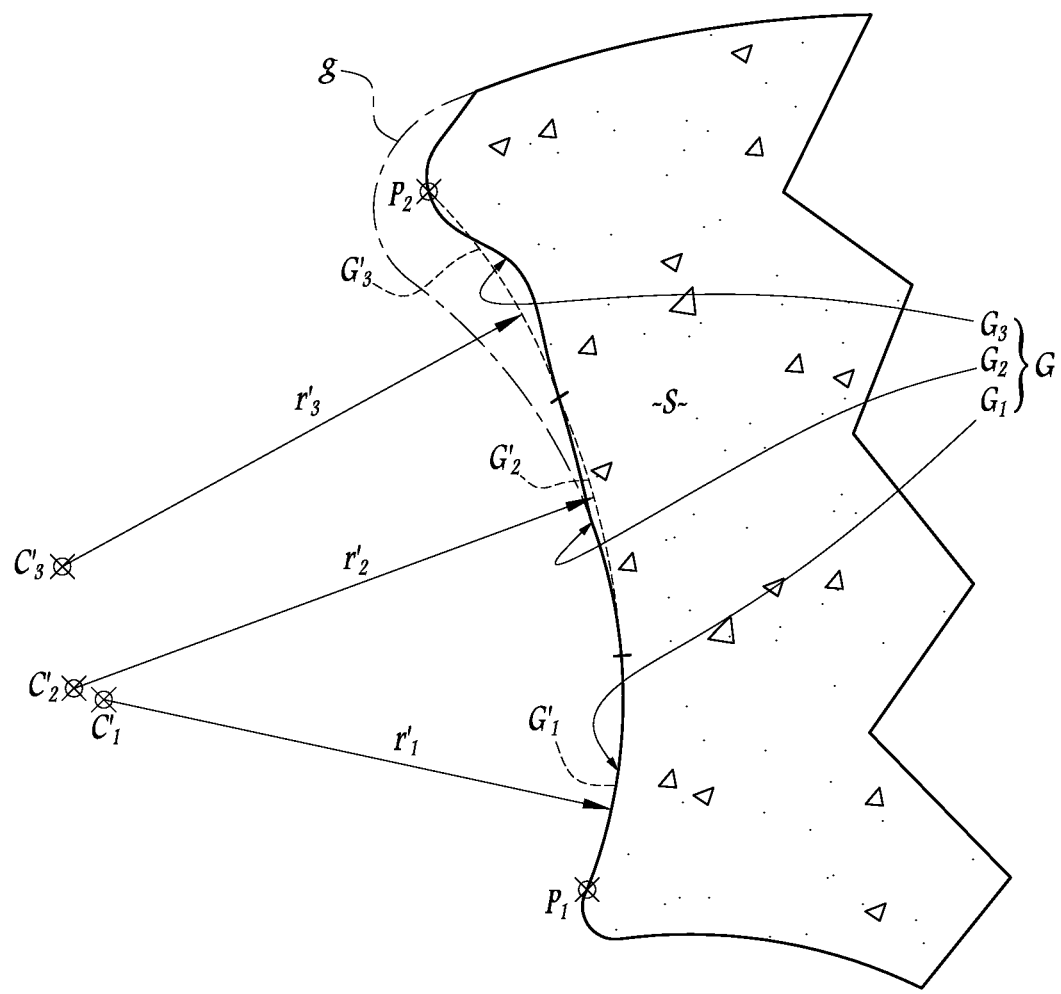
FIG. 2 is a cross-sectional view in a frontal plane with respect to the patient of the scapula during an operation with the aid of the implantation apparatus of FIG. 1.

FIG. 2 shows, in an exaggerated manner designed to facilitate understanding of the present invention, that the degeneration of the glenoid surface G is essentially situated in the upper part of the glenoid surface, particularly in the upper third of the glenoid surface. By way of comparison, the glenoid surface prior to degeneration is indicated by broken lines and by the reference sign "g". Comparison of the respective outlines of the surfaces g and G in the plane of FIG. 2 reveals that the surface G has undergone a degree of degeneration by wear that is much more pronounced in its upper part than in its lower part, which remains almost intact.

In a second step, the surgeon controls the computer 2 such that it processes the cartographic data obtained during the first operating step. Data processing means integrated in the computer 2 processes the cartographic data in a manner that is entirely pre-established, or in accordance with parameters chosen at the discretion of the surgeon, in such a way as to distribute the mapping points of the glenoid surface G into three distinct groups $G_1$, $G_2$ and $G_3$ which correspond to respective parts of the glenoid surface G and which succeed one another in a vertical direction from bottom to top. For example, the three surface parts $G_1$, $G_2$ and $G_3$ have an identical vertical dimension.

Each of the three groups of cartographic data related respectively to the surface parts $G_1$, $G_2$ and $G_3$ are then processed independently by the aforementioned data processing means in order to model an imaginary ellipsoid portion $G'_1$, $G'_2$ and $G'_3$, which is indicated by broken lines in FIG. 2 and coincides geometrically with the corresponding surface part $G_1$, $G_2$ and $G_3$. In practice, the position of the center $C'_1$, $C'_2$ and $C'_3$ and the value of the radius $r'_1$, $r'_2$ and $r'_3$ of each ellipsoid portion $G'_1$, $G'_2$ and $G'_3$, respectively, are calculated by the aforementioned data processing means in such a way that the ellipsoid portions $G'_1$, $G'_2$ and $G'_3$ passes through the largest number of mapped points for the corresponding surface part $G_1$, $G_2$ and $G_3$, respectively. Each of the ellipsoid portions $G'_1$, $G'_2$ and $G'_3$ is regarded as passing through one of the mapped points when the multidirectional deviation between the ellipsoid portion $G'_1$, $G'_2$ and $G'_3$ and the point is zero, or, at the very least, less than a predetermined value. Other mathematical methods for determining the geometric characteristics of the ellipsoid portions $G'_1$, $G'_2$ and $G'_3$ can alternatively be employed. In one embodiment, ellipsoid portions $G'_1$, $G'_2$ and $G'_3$ are spherical.

The computer 2 displays on the screen 8, for the attention of the surgeon, all or some of the modeled ellipsoid portions $G'_1$, $G'_2$ and $G'_3$, in particular their centers $C'_1$, $C'_2$ and $C'_3$, at the same time as displaying the map of the degenerative glenoid cavity as shown in FIG. 2.

It will be noted that in so far as the lower surface part $G_1$ and intermediate surface part $G_2$ are not degenerated or are only slightly degenerated, the centers $C'_1$ and $C'_2$ of their associated ellipsoid portion $G'_1$ and $G'_2$, respectively, obtained by modeling are very close to each other compared to the center $C'_3$ of the ellipsoid portion $G'_3$ modeled from the upper surface part $G_3$.

Figure 3:
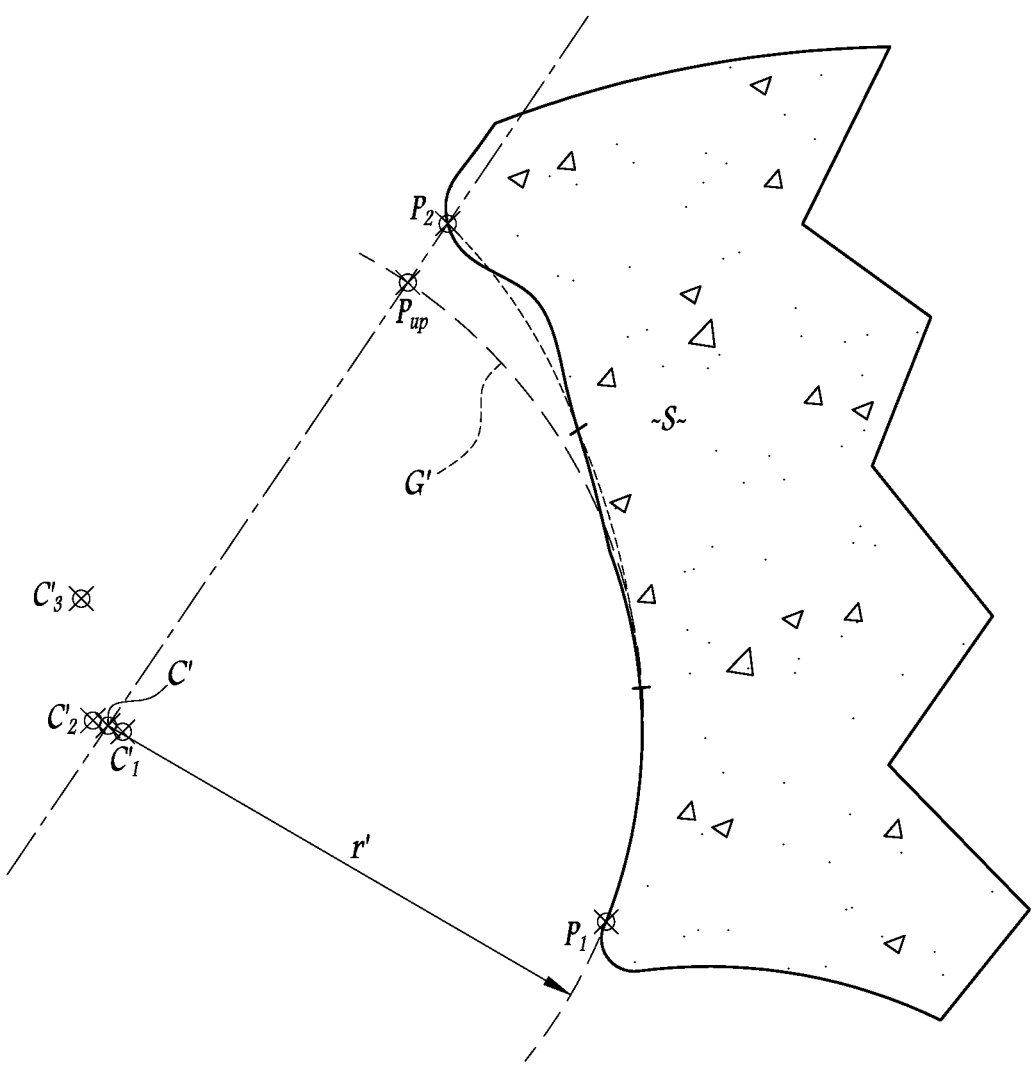
FIG. 3 is a cross-sectional view in a frontal plane with respect to the patient of the scapula during an operation with the aid of the implantation apparatus of FIG. 1.

In a third step, particularly after the surgeon checks the modeling results hitherto obtained and displayed on the screen 8, checking in particular that the modeled centers $C'_1$ and $C'_2$ are indeed close to each other by comparison to the center $C'_3$, the data processing means of the computer 2 constructs, by calculation, a spherical theoretical glenoid surface G', which is centered on a center C' and which has a radius r', of which the position and value, respectively, are calculated from the positions of the centers $C'_1$ and $C'_2$ and from the values of the radii $r'_1$ and $r'_2$. By way of example, as is illustrated in FIG. 3, the center C' is calculated as the center of mass of the centers $C'_1$ and $C'_2$, while the radius r' is calculated as the mean of the radii $r'_1$ and $r'_2$. More generally, an essential point of the present invention is that this step uses the modeled geometric data for the region of the glenoid surface G that shows the least degeneration, or the least wear, such as the lower surface part $G_1$ and intermediate surface part $G_2$. In this way, it will be appreciated that the theoretical glenoid surface G' thus calculated corresponds to a reliable estimation of the whole glenoid surface prior to degeneration. It will also be appreciated that it is possible in practice to omit calculating the geometric characteristics of the ellipsoid portion $G'_3$ if not displaying the latter on the screen 8 and not comparing it to the ellipsoid portions $G'_1$ and $G'_2$.

The computer 2 then determines the point of intersection between this theoretical glenoid surface G' and the straight line radial to the glenoid surface G' and passing through the mapping point $P_2$, that is to say the straight line passing through the points C' and $P_2$. As is shown in FIG. 3, this point of intersection is designated by $P_{up}$. It will be appreciated that this point $P_{up}$ corresponds to a reliable estimation of the upper end point of the glenoid surface prior to degeneration g. The point $P_{up}$ is displayed by the computer 2 on the screen 8 for visual monitoring by the surgeon.

Figure 4:
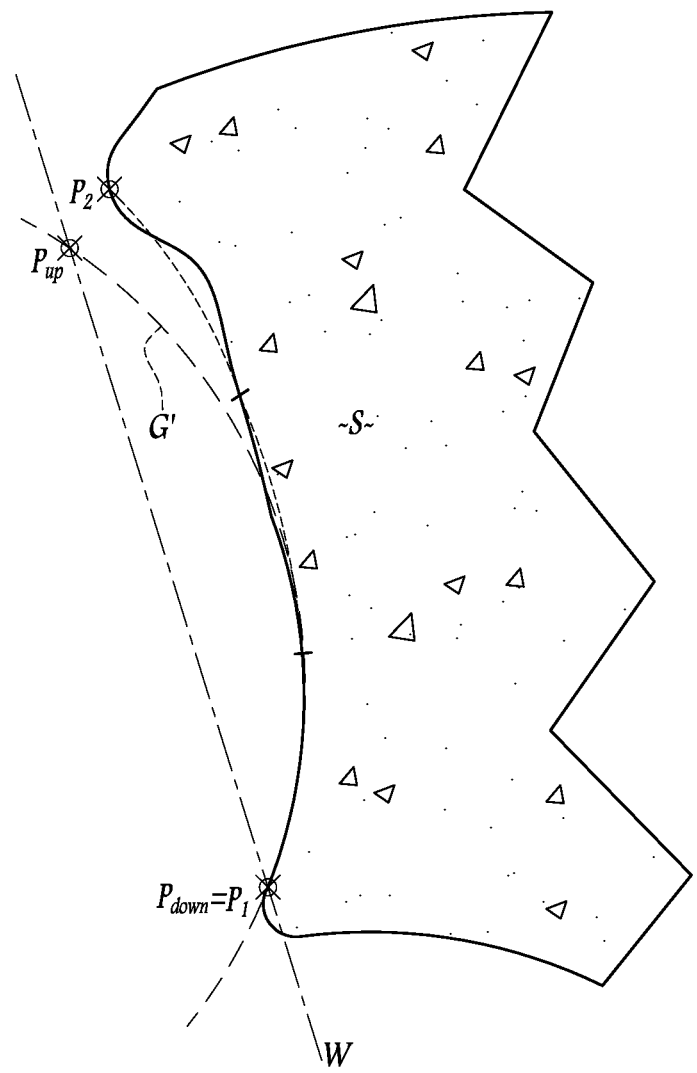
FIG. 4 is a cross-sectional view in a frontal plane with respect to the patient of the scapula during an operation with the aid of the implantation apparatus of FIG. 1.

In a fourth step, the computer 2 provides the surgeon with a display on the screen 8 that shows a plane of implantation W of the glenoid component 5 (shown in FIG. 1), the line of which can be seen in FIG. 4 passing through the aforementioned point $P_{up}$ and also through a point $P_{down}$ determined by the computer 2. The point $P_{down}$ advantageously corresponds to the mapped point $P_1$.

It is significant that the plane of implantation W corresponds to a particular plane for implanting the glenoid component 5, in the sense that it assures the surgeon that the biomechanical behavior of the glenoid component 5 will be substantially similar or identical to the behavior of the glenoid surface G prior to degeneration if the glenoid component 5 is positioned in such a way that its axis 5B (shown in FIG. 1) extends perpendicular to this plane of implantation W.

If the two points $P_{up}$ and $P_{down}$ on their own are insufficient to provide all the spatial characteristics of the plane of implantation W, the computer 2 can for this purpose use information directly supplied by the surgeon or can spatially orientate the plane W passing through the points $P_{up}$ and $P_{down}$ using the Lévigne angle, by integrating a database relating to the definition of this angle into the computer 2, which data is available from literature on orthopedics.

Thus, the method for modeling a glenoid surface of a scapula includes the successive steps of: generating cartographic data representative of points belonging to the glenoid surface that is to be modeled; distinguishing from among the cartographic data a first group of cartographic data corresponding to a first part of the glenoid surface, this first surface part being situated farthest down in the vertical direction in relation to the scapula S; calculating from the first group of cartographic data a first imaginary ellipsoid portion that coincides substantially with the first surface part; and obtaining a theoretical glenoid surface from the first ellipsoid portion. In one embodiment, the theoretical glenoid surface is composed of the first ellipsoid portion.

According to other embodiments, individually or in combination: from among the cartographic data, one or more groups of cartographic data other than the first group of cartographic data are distinguished which correspond respectively to as many surface parts of the glenoid surface that are distinct from the first surface part and that are arranged, in the vertical direction relative to the shoulder blade, following on from this first surface part and, if appropriate, one after another; one or more imaginary ellipsoid portions other than the first ellipsoid portion are calculated from the other group or groups of cartographic data, the other ellipsoid portion or portions coinciding substantially with the corresponding other surface part or surface parts; the theoretical glenoid surface is obtained from the first ellipsoid portion and from at least one of the other ellipsoid portions; in the case where the first ellipsoid portion and the other ellipsoid portion or portions correspond to sphere portions, each sphere portion is determined by calculating the position of its center and the value of its radius; the theoretical glenoid surface is spherical, the position of its center and the value of its radius being calculated respectively as the center of mass of the centers and the mean of the radii of the first ellipsoid portion and at least one of the other ellipsoid portions corresponding to the surface part or parts situated farthest down; and the first ellipsoid portion and the other ellipsoid portion or portions are determined by calculating the spatial characteristics of each ellipsoid portion in such a way that the ellipsoid portion includes, with a preset multidirectional deviation, the largest number of points of the glenoid surface which are represented by the cartographic data of the group of data related to the ellipsoid portion.

Figure 5:
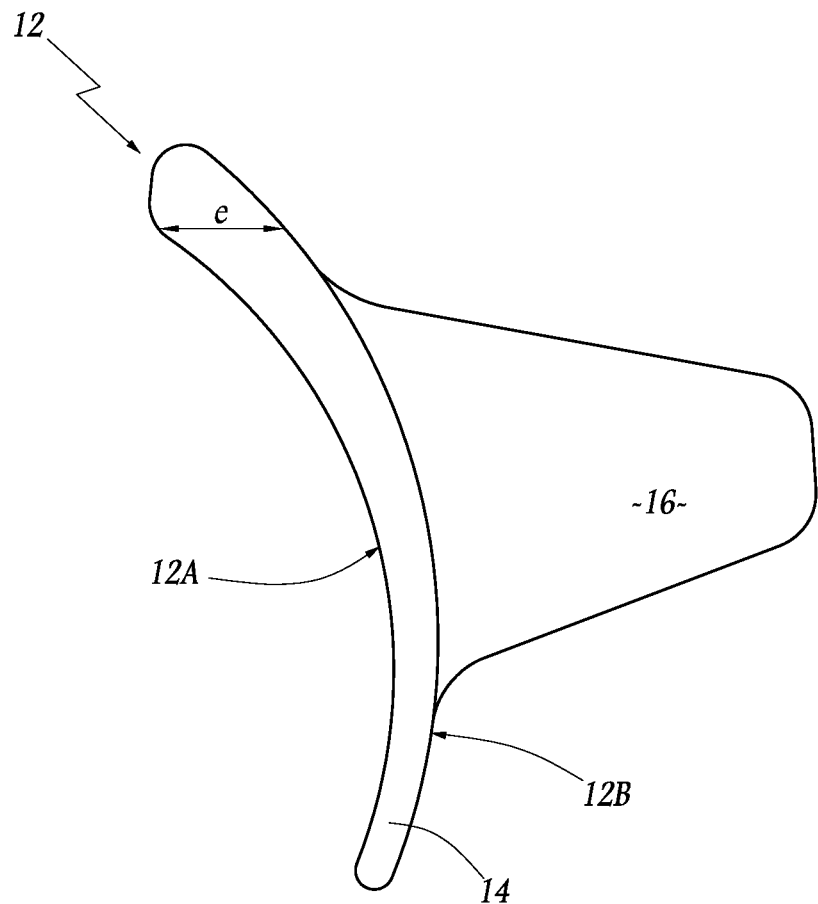
FIG. 5 is an elevational view of a glenoid component produced by a method of production according to the invention.

FIG. 5 shows a glenoid component 12 of a shoulder prosthesis which, unlike the component 5 shown in FIG. 1, is not a pre-existing part that is available from a plurality of homothetic implants. The glenoid component 12 includes a solid implant body 14, metallic or synthetic in nature, which has an overall cup shape.

One side of the body 14 is designed as an articular, concave face 12A that articulates with the humerus of a patient and supports in particular a humeral prosthetic component of the shoulder prosthesis. Most of the articular, concave face 12A, or in this case all of which, defines an articular surface designed to articulate against a substantially complementary surface (not shown in the figures) which is delimited either by the anatomical upper end of a humerus or by the humeral component of the shoulder prosthesis.

On its opposite side, the implant body 14 has a bearing face 12B which, when the glenoid component 12 is implanted, bears directly or indirectly against the osseous lateral end of a scapula S which has been prepared in advance for this purpose. In a manner known to those skilled in the art, the bearing face 12B is provided with means for anchoring the glenoid component 12 in the scapula S, for example in the form of a stem 16.

The glenoid component 12 has been "made to measure" for the scapula S in FIG. 1. Thus, the articular face 12A does not correspond to a pre-existing standard geometry but instead reproduces the theoretical glenoid surface G' provided by the computer 2 in the third operating step mentioned above. As the theoretical glenoid surface G' is a reliable estimation of the glenoid surface prior to degeneration, it will be appreciated that the articular face 12A is substantially similar, from a geometrical point of view, to the degenerated surface, which explains the use of the aforementioned expression "made to measure". The articular behavior of the glenoid component 12 on its articular face 12A is therefore almost identical to the natural behavior of the patient's shoulder prior to the degeneration of the scapula S.

Advantageously, the bearing face 12B also no longer corresponds to a pre-existing standard geometry but instead takes into account the state of degeneration of the glenoid surface G of the scapula S. In particular, the upper end part of the bearing face 12B is designed to take into account the pronounced wear in the upper part of the glenoid surface G. To do this, the thickness of the implant body 14, that is to say its dimension in a medio-lateral direction, is greater in the upper end part of the implant body 14 than in the rest of the implant body 14. The maximum value of the thickness at the upper end part of the implant body 14 being indicated by "e" in FIG. 5. The variation in thickness of the implant body 14 is determined, for example with the aid of the computer 2 from the cartographic data corresponding to the highest surface part $G_3$ (shown in FIG. 2). In this way, when the lateral end of the scapula S is prepared with a view to implantation of the glenoid component 12, the surgeon removes only a limited amount of bone substance from the lower region of the glenoid surface G, here in the area of the surface parts $G_1$ and $G_2$ (shown in FIG. 2). The amount of bone removed is just enough to take into account the small thickness of the lower part of the implant body 14, whereas the thickness of the upper part of the implant body 14 is dimensioned so as to substantially match the surface part $G_3$. In other words, contrary to conventional practice, the surgeon does not attempt to "level" the upper and most badly worn region of the glenoid surface G during its preparation, as this would lead to excessive removal of healthy areas of bone from the scapula S and would medialize the glenoid component 12, unless the implant body 14 were made thicker.

In practice, the material forming the glenoid component 12 is shaped by any technique known in the art. In the case of a glenoid component made of metal, the glenoid component can be cast and then machined. If a plastic is used, it is generally cast and then, if appropriate, rectified. In all cases, the articular face 12A and bearing face 12B are precision-worked in order to adjust them respectively to the theoretical glenoid surface G' and to the prepared lateral end of the scapula S.

The present invention relates to a surgical apparatus for implanting a glenoid component of a shoulder prosthesis including: position-finding means for spatially locating the scapula of a patient being operated on; mapping means for mapping the glenoid surface of the scapula; modeling means for implementing the modeling method defined above and thereby obtaining a theoretical glenoid surface from the cartographic data of the glenoid surface obtained by the mapping means; first means of determination for determining the spatial position of a lower reference point for implanting the glenoid component from the cartographic data obtained at the lower end of the glenoid surface by the mapping means; and means of implantation for obtaining a spatial implantation configuration of the glenoid component from at least the theoretical glenoid surface and the lower reference point.

Thus, by virtue of the theoretical glenoid surface obtained by the modeling method defined above and also by virtue of information that relates to a lower reference point that the surgeon can obtain directly from the, in principle, undamaged lower end of the degenerated glenoid surface of the patient, the surgeon can base the implantation of a glenoid component on data that is satisfactory with regards to the geometry of the glenoid surface of the patient prior to degeneration. The surgeon is thus able to improve the implantation configuration of the glenoid component and is able to do so during the surgical intervention.

In embodiments of the surgical apparatus of the present invention, the following may be used individually or in combination: a second means of determination for determining the spatial position of an upper reference point for implanting the glenoid component from cartographic data obtained at the upper end of the glenoid surface by the mapping means and from the theoretical glenoid surface; a means of implantation adapted to obtain the spatial position of a plane of implantation of the glenoid component which passes through the upper and lower reference points; the second means of determination adapted to position the upper reference point at the intersection between the theoretical glenoid surface and a straight line radial to the surface, passing through the point of the glenoid surface mapped by the mapping means and situated farthest up; and display means for displaying the glenoid surface mapped by the mapping means, the lower reference point and at least some geometric characteristics of the theoretical glenoid surface, and also, if appropriate, the upper reference point and the plane of implantation.

The present invention also relates to a surgical method for implanting a glenoid component of a shoulder prosthesis in which: the scapula of a patient being operated on is located spatially; the glenoid surface of the scapula is mapped using data acquired by tracing the scapula and/or by data extracted from pre-operative images and/or data obtained from a pre-established database; the glenoid surface is modeled in accordance with the modeling method defined above in such a way that a theoretical glenoid surface of the scapula is obtained from the cartographic data; the spatial position of a lower reference point for implanting the glenoid component is determined from the data associated with the mapping of the lower end of the glenoid surface; and the glenoid component is implanted in a spatial configuration determined from at least the theoretical glenoid surface and the lower reference point. The surgical method can be implemented by the implantation apparatus defined above.

The present invention also relates to a method for producing a glenoid component of a shoulder prosthesis for a scapula in which the glenoid surface of the scapula is modeled in accordance with the modeling method defined above, and in which the articular face of an implant body designed to articulate against a substantially complementary humeral surface is shaped in such a way that at least part of the articular face reproduces the theoretical glenoid surface supplied by the modeling method.

The production method according to the invention allows a glenoid implant to be "made to measure", in the sense that its articular face reproduces as closely as possible the glenoid surface, prior to degeneration, of the scapula that is to be fitted with a prosthesis. The articular comfort for the patient is thus enhanced.

Of course, it is advantageously possible to produce a glenoid component "made to measure" by means of the method of production according to the present invention, and then to implant the glenoid component with the aid of the implantation apparatus defined above, that is to say in accordance with the method of implantation also defined above.

Various configurations and alternatives of the implantation apparatus, of the implantation method and of the method for producing the glenoid component are also conceivable and are described below. By way of example:

- the means for finding the position of the bone of the scapula and/or of the tracer is not limited to markers that reflect infrared, markers sensitive to ultrasound or to electromagnetic fields can be used;
- it is possible to model only a single ellipsoid portion which coincides substantially with the lowest part of the glenoid surface and which will then constitute, for the purposes of the method, the theoretical glenoid surface;
- the act of determining the plane of implantation W can be made optional when the computer is capable of spatially guiding a tool for implanting the glenoid component shown in FIG. 1 such that the articular surface of the glenoid component is positioned in line with the theoretical glenoid surface, taking into account the lower reference point;
- the vertical extent of only the lowest glenoid surface part or that of each of the different glenoid surface parts succeeding one another from bottom to top can be pre-established, chosen arbitrarily by the surgeon by indicating it to the computer, or can be calculated by the computer, especially by a formula of the ratio between the extent of the part in question and the total extent of the glenoid surface; and/or
- more than three imaginary ellipsoid portions can be modeled from as many successive surface parts along the degenerated glenoid surface, the spherical theoretical glenoid surface making it possible to determine the spatial position of the upper reference point calculated from only the group or groups of cartographic data corresponding respectively to the lowest surface part or the lowest surface parts.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. An apparatus comprising:
   means for obtaining cartographic data from various locations on a scapula;
   a data processor that generates a glenoid surface model from cartographic data of the scapula supplied by the cartographic data obtaining means and pre-recorded data relating to a basic geometry of a human scapula, the cartographic data is representative of a first portion of the glenoid surface away from a more degenerated area of the glenoid surface of the scapula;
   wherein the data processor determines a thickness in a portion of a glenoid component corresponding to a second portion of the glenoid surface from the glenoid surface model and the cartographic data of the glenoid surface.

2. The apparatus of claim 1, wherein the cartographic data obtaining means comprises a tracer and a three-dimensional locating system.

3. The apparatus of claim 1, wherein the cartographic data obtaining means comprises an image scanner to generate preoperative images of the glenoid.

4. The apparatus of claim 1, wherein the glenoid surface model is generated solely from data corresponding to the first portion of the glenoid surface.

5. The apparatus of claim 4, wherein the thickness is calculated as a difference between a medio-lateral location of the glenoid surface in a more worn portion of the glenoid and a medio-lateral location of a corresponding portion of the glenoid surface model.

6. The apparatus of claim 1, wherein the first portion of the glenoid surface is situated farthest down in the vertical direction in relation to the scapula.

7. The apparatus of claim 1, wherein the more degenerated area of the glenoid surface of the scapula is situated in an upper and posterior region of the glenoid surface.

8. The apparatus of claim 1, wherein the second portion corresponds to the more degenerated area of the glenoid surface.

9. The apparatus of claim 1, further comprising a display for displaying the glenoid surface model.

10. The apparatus of claim 1, wherein the data processor is configured determine a spatial position of a plane of implantation of the glenoid component.

11. The apparatus of claim 10, wherein the spatial position of the plane of implantation of the glenoid component passes through the first portion of the glenoid surface and the more degenerated area of the glenoid surface.

12. The apparatus of claim 1, wherein the data processor determines the thickness in the second portion of the glenoid component by determining a point of intersection between the glenoid surface model and a straight line passing through a mapping point corresponding to the more degenerated area of the glenoid surface.

13. An apparatus comprising:
   means for obtaining cartographic data from various locations on a scapula, the cartographic data is representative of a first portion of the scapula away from a more degenerated area of the glenoid surface of the scapula;
   a data processor programmed to calculate an imaginary ellipsoid portion from the cartographic data representative of the first portion of the glenoid surface and pre-recorded data relating to a basic geometry of a human scapula,
   wherein the data processor is programmed to generate a glenoid surface model based at least in part on the imaginary ellipsoid portion.

14. The apparatus of claim 13, wherein the data processor is programmed to determine a thickness in a portion of a glenoid component corresponding to a second portion of the glenoid surface from the glenoid surface model and the cartographic data of the glenoid surface.

15. The apparatus of claim 13, wherein the cartographic data obtaining means comprises a tracer and a three-dimensional locating system.

16. The apparatus of claim 13, wherein the cartographic data obtaining means comprises an image scanner to generate preoperative images of the glenoid.

17. The apparatus of claim 13, wherein the glenoid surface model is generated solely from cartographic data corresponding to the first portion of the glenoid surface.

18. The apparatus of claim 13, wherein the first portion of the glenoid surface is situated in an inferior direction in relation to the scapula.

19. The apparatus of claim 13, wherein the more degenerated area of the glenoid surface of the scapula is situated in an upper and posterior region of the glenoid surface.

20. The apparatus of claim 13, further comprising a display for displaying the glenoid surface model.

21. The apparatus of claim 13, wherein the data processor is programmed to determine a spatial position of a plane of implantation of the glenoid component.

22. The apparatus of claim 21, wherein the spatial position of the plane of implantation of the glenoid component passes through the first portion of the glenoid surface and the more degenerated area of the glenoid surface.

* * * * *

UNITED STATES PATENT AND TRADEMARK OFFICE
CERTIFICATE OF CORRECTION

PATENT NO.         : 10,716,676 B2
APPLICATION NO.    : 14/576801
DATED              : July 21, 2020
INVENTOR(S)        : Alain Tornier Page 1 of 1

It is certified that error appears in the above-identified patent and that said Letters Patent is hereby corrected as shown below:

In the Specification

In Column 3, Line 10, delete "means" and insert --means.--.

In the Claims

In Column 10, Line 38, Claim 10, delete "configured determine" and insert --configured to determine--.

Signed and Sealed this
Twenty-second Day of September, 2020

Andrei Iancu
*Director of the United States Patent and Trademark Office*